(12) United States Patent
Barker et al.

(10) Patent No.: US 11,918,456 B2
(45) Date of Patent: Mar. 5, 2024

(54) DEVICES AND METHODS FOR IMPLANTING CORNEAL TISSUE

(71) Applicant: CorneaGen Inc., Seattle, WA (US)

(72) Inventors: Jerry W. Barker, Gretna, VA (US); Douglas C. Drabble, Winston-Salem, NC (US); Timothy G. Baldwin, Winston-Salem, NC (US); Yousuf Khalifa, Smyrna, GA (US)

(73) Assignee: CorneaGen, Seattle, WA (US)

( * ) Notice: Subject to any disclaimer, the term of this patent is extended or adjusted under 35 U.S.C. 154(b) by 333 days.

(21) Appl. No.: 17/240,755

(22) Filed: Apr. 26, 2021

(65) Prior Publication Data

US 2021/0315686 A1    Oct. 14, 2021

Related U.S. Application Data

(63) Continuation of application No. 15/912,990, filed on Mar. 6, 2018, now Pat. No. 10,987,212.
(Continued)

(51) Int. Cl.
*A61F 2/14* (2006.01)
*A61B 17/00* (2006.01)
(Continued)

(52) U.S. Cl.
CPC .............. *A61F 2/148* (2013.01); *A61F 2/142* (2013.01); *A61F 9/007* (2013.01);
(Continued)

(58) Field of Classification Search
CPC .......... A61F 2/148; A61F 2/142; A61F 9/007; A61F 9/0017; A61F 2/145; A61B 2017/00544; A61B 2017/00969; A61B 2017/2932; A61B 2017/305; A61B 17/3468
See application file for complete search history.

(56) References Cited

U.S. PATENT DOCUMENTS 4,325,375 A    4/1982  Nevyas
5,916,165 A    6/1999  Duchon
(Continued)

OTHER PUBLICATIONS

International Search Report for PCT/US2018/021052, dated May 14, 2018.

*Primary Examiner* — Kelly J Bekker
*Assistant Examiner* — Andrew P. Restaino
(74) *Attorney, Agent, or Firm* — Polsinelli PC

(57) ABSTRACT

A device for manipulating an implant includes a handle coupled to a guide extending from the handle to a distal end. The device includes an engagement mechanism disposed at the distal end of the guide and configured to engage an implant. The device includes a first actuator disposed on the handle and coupled to the engagement mechanism. The first actuator causes the engagement mechanism to engage the implant. The device includes an air chamber disposed in an interior chamber of the handle and configured to hold air. The device includes a lumen coupled to the air chamber and extending along the guide to the distal end. The lumen includes an air channel extending through the lumen. The device includes a second actuator disposed on the handle. The second actuator causes the air chamber to deliver the air, via the air channel, to the distal end.

14 Claims, 4 Drawing Sheets

Related U.S. Application Data

(60) Provisional application No. 62/467,319, filed on Mar. 6, 2017.

(51) Int. Cl.
    *A61B 17/29*     (2006.01)
    *A61B 17/30*     (2006.01)
    *A61F 9/007*     (2006.01)

(52) U.S. Cl.
    CPC ............... *A61B 2017/00544* (2013.01); *A61B 2017/00969* (2013.01); *A61B 2017/2932* (2013.01); *A61B 2017/305* (2013.01)

(56) References Cited

U.S. PATENT DOCUMENTS

| | | |
|---|---|---|
| 10,918,474 B2 * | 2/2021 | Liou ....................... A61F 2/148 |
| 2003/0181945 A1 | 9/2003 | Opolski et al. |
| 2006/0025813 A1 | 2/2006 | Shelton et al. |
| 2007/0239182 A1 | 10/2007 | Glines |
| 2009/0234274 A1 | 9/2009 | Luloh |
| 2010/0057093 A1 * | 3/2010 | Ide .......................... A61F 2/148 |
| | | 606/107 |
| 2010/0298864 A1 | 11/2010 | Castro |
| 2013/0085326 A1 | 4/2013 | Scheller |
| 2015/0133991 A1 | 5/2015 | Kosiorek |
| 2016/0015511 A1 | 1/2016 | Auld et al. |
| 2017/0209165 A1 | 7/2017 | Caruso |
| 2018/0064578 A1 | 3/2018 | Clauson |

\* cited by examiner

DEVICES AND METHODS FOR IMPLANTING CORNEAL TISSUE

CROSS-REFERENCE TO RELATED APPLICATIONS

This application is a continuation of U.S. Pat. No. 10,987,212, filed on Mar. 6, 2018, which claims the benefit of, and priority to, U.S. Provisional Patent Application Ser. No. 62/467,319, filed Mar. 6, 2017, the contents of each of which are incorporated herein by reference in their entirety.

BACKGROUND OF THE INVENTION

Field of the Invention

The present disclosure pertains to devices and methods for implanting tissue, and more particularly, to devices and methods for implanting donor tissue in the posterior cornea.

Description of Related Art

Endothelial cell disorders of the eye include Fuchs' endothelial dystrophy, posterior polymorphous membrane dystrophy, congenital hereditary endothelial dystrophy, bullous keratopathy, and iridocorneal endothelial (ICE) syndrome. To treat such disorders, procedures such as Descemet's Membrane Endothelial Keratoplasty (DMEK), Descemet's Stripping Endothelial Keratoplasty (DSEK), and deep lamellar endothelial keratoplasty (DLEK) replace the corneal endothelium and Descemet's membrane with a layer of donor tissue.

SUMMARY

Figure 1A:
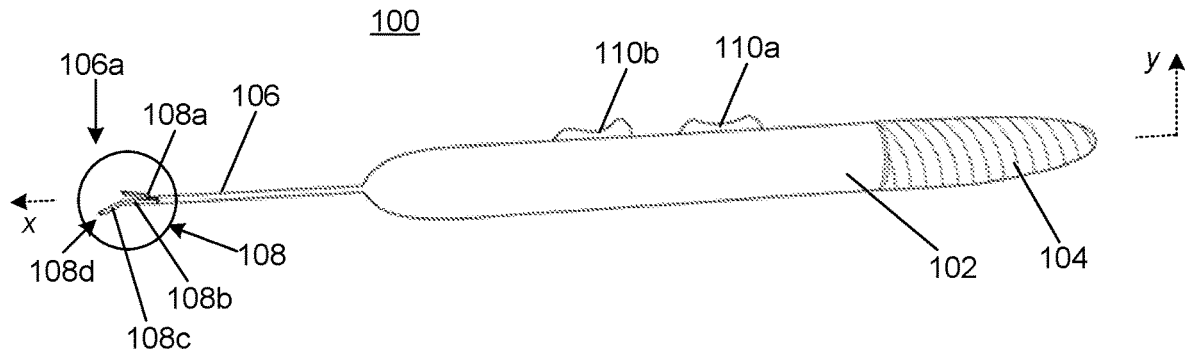
FIG. 1A illustrates an example implant device for implanting donor corneal tissue in an eye, according to aspects of the present disclosure.

According to aspects of the present disclosure, example embodiments can deliver an implant to an implant site and further manipulate the implant so that it can be received by the implant site. For instance, example embodiments can replace the corneal endothelium and Descemet's membrane to treat an endothelial cell disorder. In particular, example embodiments can deliver donor corneal tissue to the posterior cornea within an eye and further manipulate the donor corneal tissue for implantation into the posterior cornea. Such manipulation may involve flattening the donor corneal tissue so that it can be properly received by the posterior cornea.

According to an example embodiment, a device for manipulating an implant includes a handle including an interior chamber. The device includes a guide coupled to the handle and extending from the handle to a distal end. The device includes an engagement mechanism disposed at the distal end of the guide and configured to engage an implant. The device includes a first actuator disposed on the handle and coupled to the engagement mechanism. The first actuator is operable to cause the engagement mechanism to engage the implant. The device includes an air chamber disposed in the interior chamber of the handle and configured to hold air. The device includes a lumen coupled to the air chamber and extending along the guide to the distal end. The lumen includes an air channel extending through the lumen. The device includes a second actuator disposed on the handle. The second actuator is operable to cause the air chamber to deliver the air, via the air channel of the lumen, to the distal end.

According to an example embodiment, a method for operating a tissue manipulation device includes operating a first actuator on a handle of a tissue manipulation device to cause an engagement mechanism to engage a corneal implant. The engagement mechanism is disposed at a distal end of a guide extending from the handle. The method includes extending the guide into an eye and positioning the corneal implant at an implant site at a corneal posterior. The method includes operating a second actuator on the handle of the tissue manipulation device to deliver air to the corneal implant from an air chamber disposed in an interior chamber of the handle. The air is delivered via a lumen coupled to the air chamber and extending along the guide to the distal end. The method includes operating the first actuator to release the corneal implant from the engagement mechanism.

In the example embodiments above, the engagement mechanism may include a forceps having a first jaw and a second jaw, where the first actuator cause the first jaw and the second jaw to move relative to each other to engage the implant between the first jaw and the second jaw. The engagement mechanism may include a first jaw of a forceps and a part of the lumen defines a second jaw of the forceps, where the first actuator causing the first jaw to move relative to the second jaw to engage the implant between the first jaw and the second jaw.

In the example embodiments above, the air chamber may be compressible and the second actuator causes the air chamber to deliver the air by applying pressure to the air chamber. The air chamber may be formed by an air bladder formed from a pliable material.

DESCRIPTION

According to aspects of the present disclosure, example embodiments can deliver an implant to an implant site and further manipulate the implant so that it can be received by the implant site. The implant may be formed from natural tissue. In some cases, the implant may be an allograft, i.e., tissue that is transplanted between members of the same species. In other cases, the implant may be as xenograft, i.e., tissue that is transplanted between members of different species. Alternatively, the implant may be formed from a synthetic material.

For instance, example embodiments can replace the corneal endothelium and Descemet's membrane to treat an endothelial cell disorder. In particular, example embodiments can deliver donor corneal tissue to the posterior cornea within an eye and further manipulate the donor corneal tissue for implantation into the posterior cornea. Such manipulation may involve flattening the donor corneal tissue so that it can be properly received by the posterior cornea.

Figure 1B:
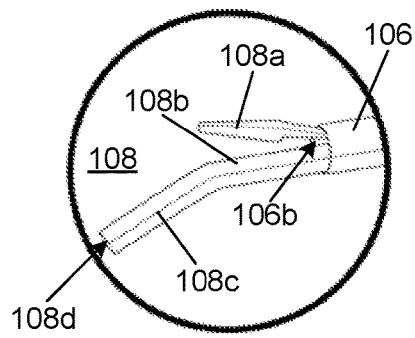
FIG. 1B illustrates a distal end of the example implant device of FIG. 1A for manipulating the donor corneal tissue, according to aspects of the present disclosure.
Figure 1C:
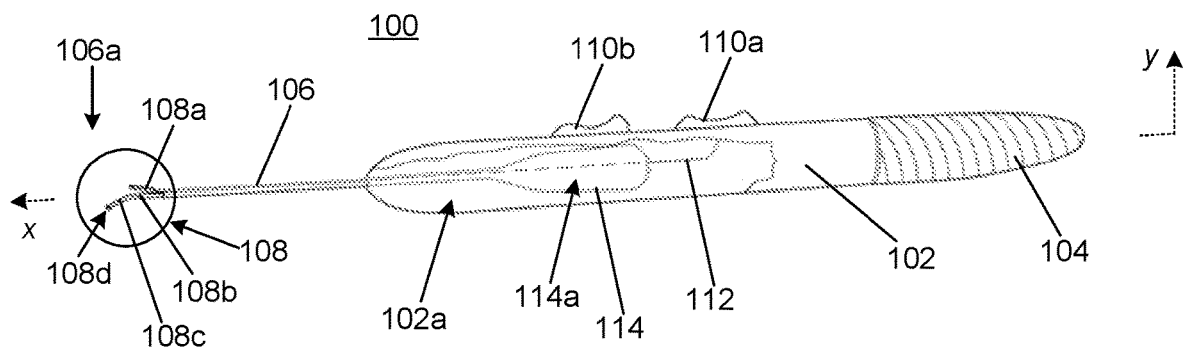
FIG. 1C illustrates a view of an interior chamber of the example implant device of FIG. 1A, according to aspects of the present disclosure.

FIGS. 1A-C illustrate an example device 100, which can be employed, for instance, to implant donor corneal tissue in the posterior cornea. The example device 100 includes a handle 102. The handle 102 may be formed from a hard plastic suitable for a surgical device. The handle 102 allows a practitioner to operate the device 100 with one hand. To provide a more secure hold by the practitioner, the handle 102 may include a grip 104. The grip 104 may include a textured surface formed with the material of the handle 102 and/or a high friction material (e.g., tacky plastic or rubber material) applied to the handle 102.

The device 100 also includes an elongate guide 106 that is coupled to the handle 102 and extends longitudinally (along the x-axis) from the handle 102 to a distal end 106a. The guide 106 may be formed from surgical stainless steel or the like. Additionally, the guide 106 includes a guide channel 106b that passes through the length of the guide 106.

The device includes an implant manipulation system 108 disposed at the distal end 106a of the guide 106. The implant manipulation system 108 is configured to manipulate an implant during an implant procedure. The components of the implant manipulation system 108 may be formed from surgical stainless steel or the like.

The implant manipulation system 108 may include a forceps device that can hold the implant. With the implant held by the forceps device, the device 100 can be maneuvered to deliver the implant to an implant site. Because the forceps device is disposed at the distal end 106b of the guide 106, the elongate guide 106 allows the device 100 to extend the implant into a body cavity where the implant site may be located.

The forceps device is formed by a first jaw 108a and a second jaw 108b. FIG. 1B illustrates the forceps in an open state, where a space is formed between the first jaw 108a and the second jaw 108b. Conversely, when the forceps are in a closed state, the first jaw 108a and the second jaw 108b are pressed against each other. As such, the device 100 can hold the implant when the forceps are in the closed state and release the implant when the forceps are in the open state. The handle 106 includes a first actuator 110a that can be operated by the practitioner to move the forceps device between open and closed states. In some cases, the first actuator 110a may be operated by pushing it into the handle 102. In other cases, the first actuator 110b may be operated by sliding it along the handle 102 (e.g., along the x-axis). In some cases, the first jaw 108a is biased away from second jaw 108b and the first actuator 110a is operated to press the first jaw 108a against the second jaw 108b. In other cases, the first jaw 108a is biased against the second jaw 108b and the first actuator is operated to move the first jaw 108a away from the second jaw 108b.

As shown in the cut-away view of FIG. 1C, the handle 102 includes an interior chamber 102a. Additionally, the guide 106 extends into the interior chamber 102a. The device 100 includes a coupling 112 that is connected to the first actuator 110a on the exterior of the handle 102. The coupling 112 extends from the first actuator 110a, through the guide channel 106b, and to the distal end 106b where it is connected to the forceps device. The coupling 112 may include a cable or linkages that cause the first jaw 108a to press against or move away from the second jaw 108b when the first actuator 110a is operated.

The implant manipulation system 108 can also deliver air to the implant to prepare the implant for implantation. As described further below, for instance, air can be employed to flatten donor corneal tissue so that it can be properly implanted into the posterior cornea. A lumen 108c extends through the guide channel 106b. The lumen 108c includes an interior air channel 108d for delivering air to the implant at the distal end 106a. As shown in FIG. 1B, a portion of the lumen 108c forms the second jaw 108b of the forceps device. Thus, the lumen 108c is a dual-purpose structure that acts as the second jaw 108b of the forceps device in addition to delivering air. The advantages of this particular configuration are described further below.

As shown in FIG. 1C, the lumen 108c extends into the interior chamber 102a of the handle 102. An air bladder 114 is disposed in the interior chamber 102a and is coupled to the lumen 108c. The air bladder 114 includes an air chamber 114a that holds air that can be delivered into the lumen 108c. The air bladder 114 may be formed from a pliable material, such as an elastomeric plastic or rubber or the like. As such, the air bladder 114 can be mechanically compressed to push the air from the air chamber 114a into the air channel 108d of the lumen 108c. The handle 106 includes a second actuator 110b that can be operated to deliver air, via the lumen 108c, to the implant at the distal end 106a. The practitioner may press the second actuator 110b into the handle 102 to cause the second actuator 110b to apply a corresponding pressure against the air bladder 114.

Figure 1D:
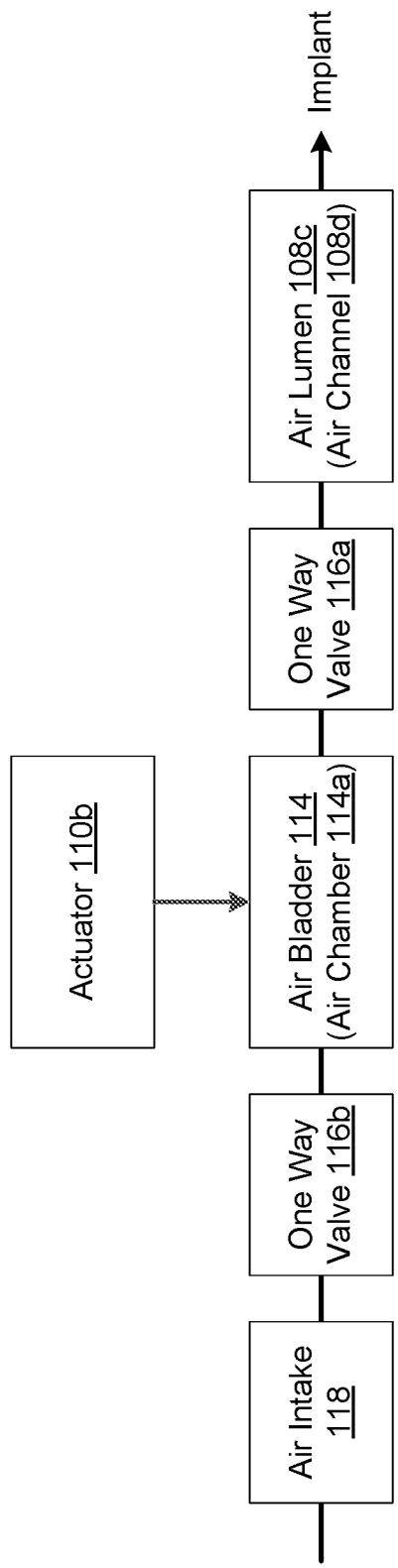
FIG. 1D illustrates aspects of an air delivery mechanism of the example implant device of FIG. 1A, according to aspects of the present disclosure.

FIG. 1D illustrates further aspects of the air delivery mechanism of the device 100. The device 100 may include a first one-way valve 116a that allows air from the air chamber 114a to move in one direction from the air bladder 114 into the air channel 108d of the lumen 108c. After the air bladder 114 is compressed from an initial shape to deliver air into the lumen 108c, the material of the air bladder 114 may cause the air bladder 114 to expand back to the initial state. Such expansion of the air bladder 114 draws air back into the air chamber 114a for additional delivery of air to the implant. The device 100 may also include a second one-way valve 116b that allows outside air to move in one direction from an air intake 118 into the air chamber 114a. Thus, the first one-way valve 116a blocks air from being drawn into the air chamber 114a when the air bladder 114 expands, and the second one-way valve 116b blocks air from being pushed through the air intake 118 when the air bladder 114 is compressed. In some cases, air filters (not shown) may also be employed, for instance at the air intake 118, to filter the air before the air is delivered to the implant.

Figure 2:
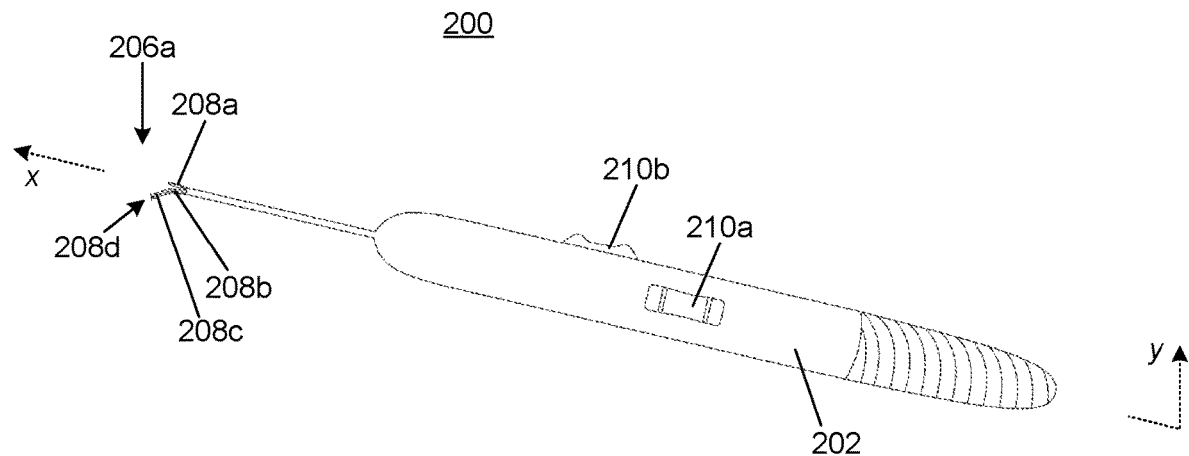
FIG. 2 illustrates another example implant device for implanting donor corneal tissue in an eye, according to aspects of the present disclosure.

Embodiments of the present disclosure are not limited to the device 100 as shown in FIGS. 1A-D. Other embodiments may employ different configurations. For instance, FIG. 2 illustrates another example device 200, which is similar in most respects to the example device 100. Like the example device 100, the device 200 includes a handle 202 with a first actuator 210a to operate a forceps device defined by a first jaw 208a and a second jaw 208b at a distal end 206a. Additionally, the handle 202 includes a second actuator 210b to deliver air to the distal end 206a via an air channel 208d in a lumen 208c. A portion of the lumen 208c also forms the second jaw 208b of the forceps device.

Although the device 100 can be operated with one hand, operation of the device 200 with one hand is further facilitated by the configuration of the handle 202. In particular, the first actuator 210a and the second actuator 210b have relative positions that allow the practitioner to simultaneously access the first actuator 210a with a thumb and the second actuator 210b with an index finger. In other words, the practitioner is not required to re-grasp and re-orient his/her hand on the handle 202 for alternating operation of the first actuator 210a and the second actuator 210b.

As shown in FIG. 2, the second actuator 210b is spaced more distally (closer to the distal end 206a along the x-axis) than the first actuator 210a to accommodate the longer reach of an index finger. In addition, the first actuator 210a is spaced further from the second actuator 210b along the periphery of the handle 202 (where the periphery of the handle 202 is defined on a plane intersecting the x-axis) to accommodate the transverse distance between the thumb and the index finger. In alternative embodiments, the first actuator 210a may be positioned for operation by the index finger while the second actuator 210 may be positioned for operation by the thumb. Furthermore, while the device 200 shown in FIG. 2 may be configured for right-handed use, alternative embodiments may be configured for left-handed use.

As described above, the features of the example devices 100 and 200 are provided in a single integrated unit. Thus, the devices 100 and 200 can be more easily and conveniently operated without relying on additional external devices/systems.

Additionally, the features of the devices 100 and 200 are provided by mechanical components. As such, the devices 100 and 200 can be operated without electric/electronic components and power sources. Without electric/electronic components and power sources, the devices 100 and 200 may be less likely to malfunction. In addition, the devices 100 and 200 can be produced in a more efficient and cost-effective manner. The low cost of production makes it more feasible to employ the devices 100, 200 as disposable, one-time use devices. In some cases, however, the devices 100 and 200 may be sterilized for repeated use.

In general, example embodiments can deliver an implant to an implant site and further manipulate the implant so that it can be received by the implant site. Although the devices described herein may employ a forceps device to hold the implant, other embodiments may additionally or alternatively include other types of engagement mechanisms to manipulate the implant. For instance, some embodiments may employ needles, hooks, blades, and/or other tools.

In addition, although the devices described herein may employ an air bladder to apply air to the implant, other embodiments may employ other types of air containers that can be operated to release air. For instance, some embodiments may air pistons, while other embodiments may employ pressurized cartridges with actuated valves to release air from the cartridge. In alternative embodiments, it is contemplated that a non-air gas may be delivered to the implant.

Furthermore, although the lumen may pass through the guide channel in the devices described herein, the lumen in other embodiments may extend externally along the guide.

Figure 3A:
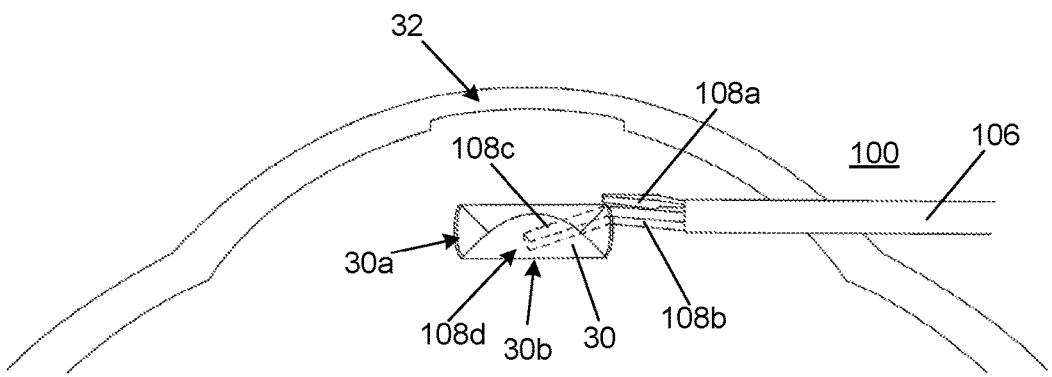
FIG. 3A illustrates aspects of an example implementation of the example implant device of FIG. 1A, according to aspects of the present disclosure.
Figure 3B:
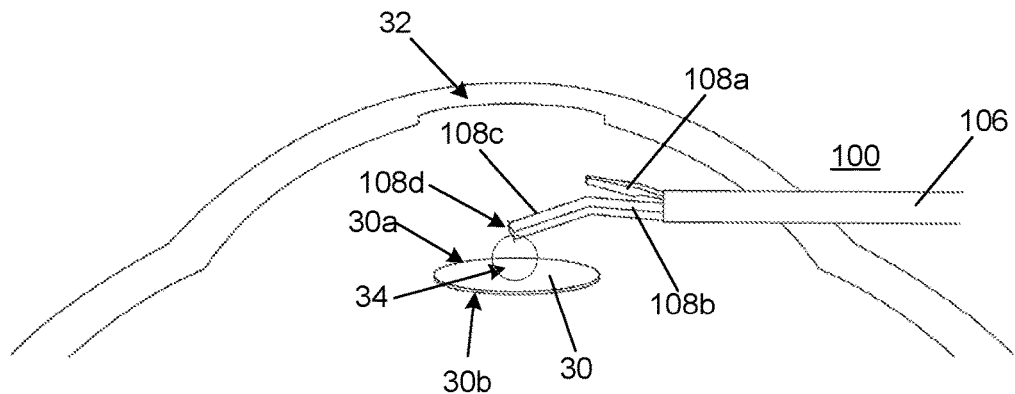
FIG. 3B illustrates further aspects of the example implementation of FIG. 3A, according to aspects of the present disclosure.

FIGS. 3A-B illustrate an example implementation of the device 100 described above. (It is contemplated, however, that the device 200 may be alternatively employed in the example implementation.) As shown in FIGS. 3A-B, the device 100 may be employed to treat an endothelial cell disorder by replacing the corneal endothelium and Deseemet's membrane.

The device 100 can deliver donor corneal tissue 30 to the posterior cornea 32 within an eye. In particular, with the handle 102 in one hand, a practitioner may operate the actuator 110a to open and close the jaws 108a and 108b to engage an edge of the donor corneal tissue 30 outside the eye. The tissue 30 may include a Descemet's membrane 30a as well as an endothelial layer 30b. The tissue 30 may roll into a scroll or form a folded shape with the endothelial layer 30b facing outwardly as shown in FIG. 3A. The forceps device holds the tissue 30 so that the fist jaw 108a is positioned against the endothelial layer 30b, while the second jaw 108b is positioned against the Descemet's membrane 30a inside the scroll or folded shape.

With the tissue 30 securely held between the jaws 108a and 108b, the practitioner can maneuver the device 100 to move the tissue 30 through an incision in the eye and to the implant site at the posterior cornea 32. The elongate guide 106 allows the practitioner to extend the tissue 30 into the eye.

After the donor corneal tissue 30 is delivered to the implant site, the practitioner can operate the actuator 110b to deliver a volume of air through the air channel 108d to the distal end 106a. In this example, compression of the air bladder 114 via the actuator 210b may deliver approximately 0.25 cm$^3$ to approximately 0.50 cm$^3$ of air. Because a portion of the lumen 108c also forms the second jaw 108b of the forceps device, operation of the forceps device advantageously positions the lumen 108c inside the scroll or folded shape and allows the volume air is also delivered inside the scroll or folded shape.

As shown in FIG. 3B, the volume of air applies a pressure in an area 34 against the Descemet's membrane 30a and causes the tissue 30 to unroll or unfold. In this way, the device 100 can employ air to flatten the tissue 30 so that it can be properly received by the posterior cornea. The lumen 108c is configured with a length that delivers the air to an area 34 where the air more effectively flattens the tissue 30. Once the tissue 30 is flattened, the tissue 30 is ready for further steps in the implantation process. The practitioner can thus operate the first actuator 110a to release the tissue 30 and maneuver the device 100 to retract the device 100 from the eye. Further steps in the implantation process may include removal of the air delivered by the device 100 so that the implant site can receive the tissue 30.

Figure 4:
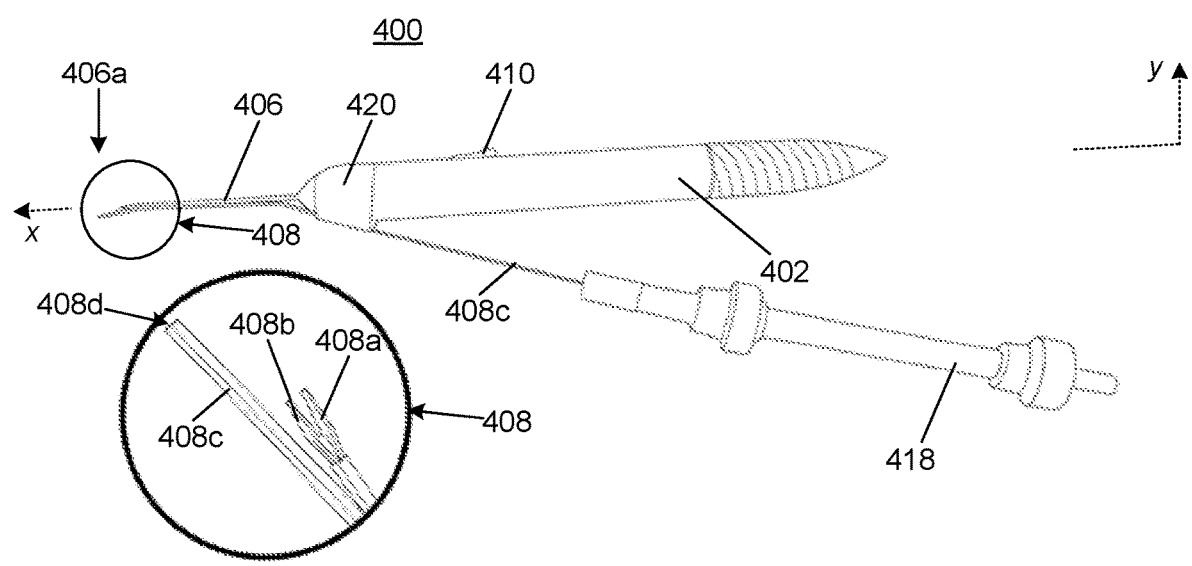
FIG. 4 illustrates yet another example implant device for implanting donor corneal tissue in an eye, according to aspects of the present disclosure.

FIG. 4 illustrates another example device 400 for manipulating an implant. Similar to the devices 100 and 200 above, the device 400 includes a handle 402 and a guide 406 that extends from the handle 402 to a distal end 406a. Like the devices 100 and 200, the device 400 can be employed, for instance, to deliver donor corneal tissue to the posterior cornea within the eye and flatten the donor corneal tissue so that it can be properly received by the posterior cornea.

The device 400, however, demonstrates that various configurations are contemplated for the forceps device and/or air delivery mechanism according to aspects of the present disclosure. In particular, the device 400 includes an implant manipulation system 408 that differs from those of the devices 100 and 200. The implant manipulation system 408 does not employ a lumen that passes through the guide 106 and delivers air from an air bladder disposed in the handle 402. Rather, the implant manipulation system 408 includes an external lumen 408c that is coupled to an external air source (not shown) via a connector 418. The external lumen 408c is coupled to the handle 402 via a coupling 420, such as a band, tape, or the like. The external lumen 408c extends along the guide 406 to the distal end 406a. A channel 408d passing through the external lumen 408c can thus deliver air to the implant. Because the air is delivered from an external air source, the handle 402 does not include an actuator for operating the air delivery, in contrast to the handles 102 and 202 above. In alternative embodiments, the external lumen 408c is coupled, via the connector 418, to an external source that provides a non-air gas.

As shown in FIG. 4, the implant manipulation system 408 also includes a forceps device for holding the implant. The forceps device includes a first jaw 408a and a second jaw 408b. In contrast to the second jaws 108b and 208b above, however, the second jaw 408b is a structure separate from the lumen 408c. The forceps device in the device 400 is operated by an actuator 410 on the handle 402.

In alternative embodiments, the connector 418 of the device 400 may be coupled to an external liquid source so that the external lumen 408c can deliver a liquid to the implant site. Indeed, it is contemplated that the devices 100 and 200 described above may additionally include an external lumen similar to the external lumen 408c of device 400. This external lumen may be coupled to the handle 102 or 202 and connected to an external liquid source to deliver liquid to the implant site.

Although the example implementations described herein may involve manipulating donor corneal tissue to replace the endothelium and Descemet's membrane, it is contemplated that aspects of the present disclosure may be employed in other procedures on the eye and other parts of the body.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A method for operating a tissue manipulation device, comprising:
    operating a first actuator on a handle of the tissue manipulation device to cause forceps to engage a corneal implant, the forceps being disposed at an end of a guide extending from the handle;
    extending the guide into an eye and positioning the corneal implant at an implant site at a corneal posterior;
    operating a second actuator on the handle of the tissue manipulation device to deliver air to the corneal implant from an air chamber disposed in an interior chamber of the handle, the air being delivered via an air channel coupled to the air chamber and extending along the guide to the end; and
    operating the first actuator to release the corneal implant from the forceps.

2. The method of claim 1, wherein the forceps include a first jaw and a second jaw, the first actuator causing the first jaw and the second jaw to move relative to each other to engage the corneal implant between the first jaw and the second jaw.

3. The method of claim 1, wherein the forceps include a first jaw and a second jaw, the second jaw formed on a dual-purpose structure having at least a portion of the air channel disposed therein, the first actuator causing the first jaw to move relative to the second jaw to engage the corneal implant between the first jaw and the second jaw.

4. The method of claim 1, wherein the air chamber is formed by an air bladder formed from a pliable material and the second actuator causes the air chamber to deliver the air by applying pressure to and compressing the air chamber.

5. The method of claim 4, wherein the air chamber expands to draw additional air from outside the air chamber after the second actuator applies the pressure to the air chamber to deliver the air from the air chamber, and the method further comprising operating the second actuator to deliver the additional air to the corneal implant via the air channel.

6. The method of claim 1, wherein operating the second actuator causes the air chamber to deliver approximately 0.25 cm$^3$ to approximately 0.50 cm$^3$ of the air to the corneal implant.

7. The method of claim 1, wherein the guide includes a guide channel extending through the guide, the air channel extends through the guide channel, and the forceps are coupled to the first actuator via a cable or one or more linkages extending through the guide channel.

8. The method of claim 1, wherein the handle extends from the guide along a longitudinal axis, the first actuator is positioned a distance from the second actuator along the longitudinal axis, and the first actuator is positioned a further distance from the second actuator along a periphery of the handle, the periphery of the handle being defined on a plane intersecting the longitudinal axis.

9. The method of claim 1, wherein the corneal implant rolls into a scroll or folded shape when engaged by the forceps and the delivered air flattens the corneal implant.

10. The method of claim 3, wherein the dual-purpose structure defines a distal end of the tissue manipulation device, the second jaw formed on a portion of the dual-purpose structure such that the forceps are spaced from the distal end.

11. The method of claim 3, wherein the dual-purpose structure defines a distal end of the tissue manipulation device, the air channel extending to the distal end.

12. The method of claim 5, wherein the air chamber includes a first one-way valve and a second one-way valve, the first one-way valve allowing the air to be delivered from the air chamber into the air channel, the second one-way valve allowing the additional air to be drawn into the air chamber.

13. The method of claim 1, further comprising delivering liquid from an external liquid source to the end of the guide.

14. The method of claim 13, wherein the liquid is delivered via an additional lumen, the additional lumen extending from the handle to the external liquid source.

* * * * *